(12) United States Patent
Sandvoss

(10) Patent No.: US 7,044,634 B2
(45) Date of Patent: May 16, 2006

(54) THERMOGRAPHY METHOD

(76) Inventor: Rolf Sandvoss, Grevenbrolcher Strasse 37, Köln (DE) 50829

( * ) Notice: Subject to any disclaimer, the term of this patent is extended or adjusted under 35 U.S.C. 154(b) by 0 days.

(21) Appl. No.: 10/470,241

(22) PCT Filed: Jan. 24, 2002

(86) PCT No.: PCT/DE02/00235

§ 371 (c)(1),
(2), (4) Date: Dec. 22, 2003

(87) PCT Pub. No.: WO02/059587

PCT Pub. Date: Aug. 1, 2002

(65) Prior Publication Data

US 2004/0081221 A1    Apr. 29, 2004

(30) Foreign Application Priority Data

Jan. 26, 2001 (DE) ............... 101 03 689
Nov. 2, 2001 (DE) ............... 101 53 592

(51) Int. Cl.
G01N 25/00 (2006.01)
G01J 5/00 (2006.01)

(52) U.S. Cl. ............... 374/5; 374/57; 374/121; 374/124

(58) Field of Classification Search ............ 374/5, 374/4, 121, 45, 57, 124, 137, 161; 356/43, 356/237.2; 250/339.06, 341.6, 339.04, 334, 250/341.1
See application file for complete search history.

(56) References Cited

U.S. PATENT DOCUMENTS

| | | | | |
|---|---|---|---|---|
| 4,868,768 A | * | 9/1989 | Draggoo et al. | 250/341.6 |
| 4,965,451 A | * | 10/1990 | Solter | 374/5 |
| 5,111,048 A | * | 5/1992 | Devitt et al. | 374/5 |
| 5,250,809 A | * | 10/1993 | Nakata et al. | 374/5 |
| 5,304,809 A | | 4/1994 | Wickersheim | |
| 5,376,793 A | | 12/1994 | Lesniak | |
| 5,582,485 A | | 12/1996 | Lesniak | |

(Continued)

FOREIGN PATENT DOCUMENTS

GB    2 164 147 A    3/1986

(Continued)

Primary Examiner—Diego Gutierrez
Assistant Examiner—Mirellys Jagan
(74) Attorney, Agent, or Firm—Akerman Senterfitt

(57) ABSTRACT

The invention relates to a method and to a device (1) for testing materials by determining and displaying as an image temperature differences above a threshold value on the surface of test objects (8). In a first step, a camera for determining and displaying as an image the temperature differences above a threshold value is used to determine the temperatures of object elements (22) within a test area (14) of the test object (8) facing the camera. The test area (14) is then provided with heat by beam (4) in such a manner that the temperature of the surface of the test object (8) rises in the test area (14) by at least of the threshold value. The object elements (22) are displayed as image elements in such a manner that the temperature differences above the threshold value between the object elements (22) are visible. The cool-down of the test area (14) is indicated by means of the image elements (20).

7 Claims, 4 Drawing Sheets

U.S. PATENT DOCUMENTS

| | | |
|---|---|---|
| 6,013,915 A | 1/2000 | Watkins |
| 6,019,504 A * | 2/2000 | Adams ......................... 374/5 |
| 6,419,387 B1 * | 7/2002 | Legrandjacques et al. ..... 374/5 |
| 6,840,667 B1 * | 1/2005 | Schlagheck et al. ........... 374/5 |
| 2002/0027941 A1 * | 3/2002 | Schlagheck et al. ........... 374/5 |
| 2002/0167987 A1 * | 11/2002 | Schlagheck et al. ........... 374/5 |
| 2004/0228432 A1 * | 11/2004 | Glass et al. .................... 374/5 |

FOREIGN PATENT DOCUMENTS

| | | |
|---|---|---|
| GB | 2 220 085 A | 12/1989 |
| JP | 60098321 A * | 6/1985 |
| JP | 62098243 A * | 5/1987 |
| JP | 63063959 A * | 3/1988 |
| JP | 05307013 A * | 11/1993 |

* cited by examiner

THERMOGRAPHY METHOD

The invention relates to a method and to a device for testing material properties using an active thermographic method.

Numerous devices for testing materials, i.e. test objects shaped as solid bodies, are known and improved. Particularly advantageous methods include methods for the non-destructive testing of materials, as these testing methods do not affect the usability of the test object. A non-destructive overall test of different constructional parts provides a higher degree of security with respect to the resulting evaluation compared with random sample tests. Such non-destructive tests include partial areas of the test objects (e.g. the surface) as well as their entire cross-section. Physical material properties such as x-ray absorption, reflection of ultrasonic waves, sound emission, or magnetic properties are utilised to determine defects (e.g. cracks, blowholes, or slag inclusions) and segregated zones. Known non-destructive testing methods include x-ray and gamma ray testing, ultrasonic testing, magnetic powder testing as well as electric and magnetic investigations.

The utilisation of thermographic systems has developed as a non-destructive testing method. Thermography uses the infrared wave range. On the shortwave side, the infrared range starts with dark red near the limit of perception of visible light while on the other, long-wave side blending into the microwave range having wavelengths at a magnitude of millimeters. A thermosensitive camera allows to measure the infrared radiation emitted by an object and to display this radiation as a visible image. As radiation is a function of the surface temperature of the object, the camera is able to precisely calculate and display this temperature. This method is used, for example, for determining cracks or leaks in vessels. If for example a gas flows out of a vessel through a leak, this can be determined by means of measuring the emitted infrared radiation provided that there is a temperature difference between the gas and the wall of the vessel.

It is the object of the present invention to provide a non-destructive testing method which can be used quickly and easily. This method shall allow the determination of inhomogenities (such as material differences, inclusions), as well as material defects such as cracks and breaks. Said method shall be quick and easy to use and allow a precise investigation of individual, even small, testing areas.

According to the present invention, this object is accomplished by a testing method for materials using a camera capable of recording temperature differences above a threshold value for determining and displaying as an image temperature differences on surfaces of test objects, wherein
a) the individual temperatures of object elements within a test area of the test object facing the camera are determined and displayed, and
b) the temperature of said object elements is, precisely within a test area to be defined in any shape, actively changed by means of a focussed light beam, especially a laser beam, in such a manner that the temperature of the surface of the test object positioned in the test area changes by at least the amount of the threshold value, and
c) the object elements the temperature of which has been changed are displayed as image elements in such a manner that their individual temperature behaviour becomes discernible due to the temperature change, and
d) preferably the further temperature change of the test area is displayed by means of the image elements.

Further, the object of the invention is accomplished by a device for testing materials by a camera to determine and display as an image temperature differences above a threshold, and by a light source, particularly a laser device, which emits a light or laser beam in such a manner that it hits a surface of a test object and raises the temperature of a test area facing the camera by at least the amount of the threshold value.

The invention is based on the perception that it is the visualisation of the cooling-down process of a surface rather than the measurement of the absolute temperature of the test object which allows conclusions regarding the material properties. Essential material differences within an area to be tested may be derived from the speed at which heat is conducted through the material or through different materials and defects. For this purpose, it is necessary to not only, as was typical up to now, passively check the temperature of the test object but to actively supply heat. Thus, the method according to the present invention is an active thermographic method.

This method is especially suitable for checking composite materials such as glass-fibre plastic or laminate. It is also possible without problems to reliably detect defects in homogeneous materials.

In this process, a thermographic camera is used for example to first determining the temperature of the surface to be checked of the test object. At this time, the test object is advantageously in a state of thermal balance with its environment. A laser beam is used to evenly heat the surface area to be tested on the test object with the thermographic camera recording the temperature increase of the surface. The surface temperature has to be increased by at least the minimum temperature difference (threshold value) which can be determined and displayed by the camera, although an increase by a multiple of the threshold value, for example by 10 Kelvin in case of a 0.1 Kelvin threshold value, may result in more revealing information and a higher resolution of the display of the measuring result. The thermographic camera allows to directly observe the discharge of the irradiated heat, i.e. the cooling-down of the surface. The image display provided by the camera allows to quickly and clearly determine irregularities in the material of the test object which affect heat conduction. Here, it may be advantageous to use a thermographic camera which produces coloured images, but a grey-scale representation may be preferred as well.

In contrast to supplying heat to the test object by a state-of-the-art method, for example using a heat radiator or a halogen lamp, the use of a laser beam for heating according to the present invention allows an extremely precise, homogeneous heat supply across the entire test area. This on the one hand due to the relatively small, punctual heat transmission in the area of the focal spot which may, for example, amount to only 2 to 3 cm², and on the other hand due to the precise guiding of the focal spot towards the borders of the test area. In contrast to heating the test area with a heat radiator or a quartz lamp, a laser beam allows heat supply exactly within the borders of a test area of any shape due to the high energy density, the small focal spot and mainly due to the low dispersion of the laser beam. For example, only a definite and even asymmetrical area of a test object may be selected and heated. The laser device can be programmed in such a manner that the laser beam scans any shape. It is particularly advantageous that in contrast to the state of the art the adjacent areas are not included in the heating by the laser beam. This is beneficial when the adjacent areas consist of heat-sensitive material or when these areas are to be checked afterwards at the same temperature, if possible.

The laser beam may for example be guided on a meander path across the test area while observing the outer borders of the test area so precisely that a sharp borderline with the not actively heated adjacent area is achieved. The heat to be supplied may be varied by the intensity of the laser or by the duration of heat application and/or the speed of the moving laser beam. The laser beam may be guided across the test area at a speed of, for example, between 1 and 10,000 mm per second. Due to the targeted heat application onto the surface within milliseconds, any disturbances or material properties of the component to be tested become visible immediately on the screen of the thermographic camera and/or another screen connected thereto. The quality of the measuring results obtained exceeds by far the quality of measuring results obtained by systems of the state of the art, mainly due to the even heating of the test object across the entire test area.

An observation using the thermographic camera over a longer period of time further allows a spatial evaluation of the material. The position of deep defects can be derived from the surface temperatures or temperature differences changing in the course of that period. It is possible for example to generate a computer-aided three-dimensional image of the test object. The measuring results can also be influenced by heating the surface to be tested once again after the first heating process.

The fast, short-time heat application by means of a laser entails only a short-time heating for some milliseconds which may be beneficial in case of heat-sensitive materials.

Due to the advancing semiconductor technology, the heat measuring cameras (thermographic cameras) now available have reached such a degree of precision or sensitivity that even smallest temperature differences (<100 mK) can be detected. The heat flow discharged into the test object can be displayed on a screen at an appropriate high resolution. Thus, even minuscule variations or material differences can be detected. It has proved especially beneficial to observe the temperature changes on the screen in real time. In addition, these live images may be digitally stored as a sequence similar to a video film using appropriate software on a computer for being further processed later by additional software to obtain the desired representation and/or results. For instance, a good representation of the temperature change of the test area can be obtained by playing a film sequence at a higher speed several times or infinitely (so-called loop play). An appropriately high frame repeat rate provides a practically immobile image in which the components or material differences affecting the heat discharge are well visible. It is also possible in a good and easy manner to put digitised data generated in this manner into archives. For such methods, the so-called IMG format offers itself.

Depending upon the aim and the test object, it is also possible to heat the rear side of the test object so that the thermographic camera records the heat flow from the side of the test object facing away from the thermographic camera towards the thermographic camera based on the heat development on the surface facing the thermographic camera.

Simultaneous heating and temperature measurement are possible as a thermographic camera is "blind" with regard to visible light. In contrast to conventional systems, it is also imaginable that the laser device is positioned quite next to the thermographic camera or even directly connected with the thermographic camera, for example by means of rods. In contrast to a conventional heat source such as a halogen lamp, a temperature influence on the thermographic camera caused by the vicinity of the laser device is practically excluded or at least significantly reduced.

It is possible as well to improve the investigation of the test object by, for example, previously determining the heat absorption capability of the test area. For this purpose, the entire test area is at first heated for a short time followed by recording the reflected image of the test area by means of a CCD camera. The resulting image (photograph) shows high reflection areas bright and low reflection areas darker. The subsequent heat supply by the laser which in the end is to serve the investigation of the test area, may then be properly adjusted through the intensity or resting duration of the laser beam to achieve an even heating of the deeper layers independent of the surface of the test area.

The reflected share and thus the absorbed share of a first heating for later adjusting the supply of heat may also be measured by the thermographic camera itself. Immediately after the first heating, the test area is recorded by the thermographic camera. The resulting image also shows those spots or portions of the test area which reflect or carry away heat to a larger or smaller extent.

It is further imaginable to apply a layer of coal or graphite powder onto the entire test area prior to the investigation. Such coating equalises the reflection capability of the test area and can quickly and easily be removed afterwards. This method is, for example, particularly suitable for small test objects. Any other suitable material may be used for such coating as well.

A major advantage of the use of a laser beam according to the present invention is that even large areas may be centrally heated. As the laser beam has relatively low losses of power even at large distances, a single, central positioning of the laser device will be sufficient. Large ship hulls, for example, do not require additional expenses for ensuring an even heat supply (such as the installation of accessible scaffoldings).

Another major advantage of the method according to the-present invention is that it allows a reliable determination of the quality of spot weld seams. Weld points occurring in spot welding have a high heat conductivity level and carry off heat supplied very quickly. Sheet metal being unjoined or poorly joined and characterised by non-joining weld points or air inclusions carry off less heat which can be easily detected by a thermographic camera. The use of a laser beam allows a punctual, small-area investigation of weld points which is especially advantageous in mass production. It is possible, for example, to heat spot weld seams by means of a laser having a defined capacity and resting duration on the weld point and to be filmed afterwards. If a checked weld point has a colour in the thermographic image which deviates from a rated value, an alarm or a production stop may be prompted.

Likewise, a check of linear weld seams is possible to quickly and simply detect an interruption of the weld seam.

The method or device according to the present invention is particularly suitable for checking boat hulls made of glass-fibre plastic (GFP). It was found that salt or fresh water ingress into or penetrate more or less protected glass-fibre laminate. This happens depending upon the temperature, age, and composition of the media water/GFP. As a consequence, delamination, water ingress and finally the destruction of the boat hull may occur. The method or device according to the present invention allow to prove this unwanted change of the state of the boat hull in any stage. Thus, this method helps to evaluate the state of a hull and/or to prove the aforementioned deficiencies and may be used to make decisions about the value of a boat, in particular after accidents and the like. It is possible as well to use the method according to the present invention to easily check the flawless quality of the boat hull. It is also imaginable that the laser beam used for the investigation is used to directly obliterate the osmotic damage found or to cut the material by adjusting or varying its power.

The invention may similarly be used to check steel objects such as motorcars or aeroplanes. It is possible, for example, to externally and contactlessly check car bodies for invisible repairs covered by paint, due to the differing heat conductivity of steel and filler, the latter becomes clearly visible when the method according to the present invention is used.

Another interesting utilisation area of the method according to the present invention is the marking and/or identification of objects. Cars or boats may, for example, comprise a marker such as an identification number at any place beneath their paint which marker can quickly and easily be checked using the method according to the present invention. It is imaginable, for example, that motorcars comprise such a marker on their roof which during the passage beneath a measuring point (for instance at national borders) could quickly and reliably identified from above. Small markers could be checked during vehicle spot-checks by manual devices. It is explicitly pointed to the fact that teachings of marking and identifying are regarded as independent inventions and that a partial application is reserved independent of the teachings of the present invention.

With regard to checking the bond of composite materials or laminates, it is imaginable to firstly heat the material to be tested on a production line by means of a laser beam followed by determining the temperature gradient through the composite plate using one or several thermographic cameras moving parallel to the production conveyor line. Improper bonding and air inclusions may thus be detected during or shortly after the manufacturing process and be eliminated immediately.

The aforementioned application examples represent only a few opportunities offered by the method or device according to the present invention. Further advantageous design features are specified in the description of the figures and in the dependent claims. Illustrated in:

Figure 1:
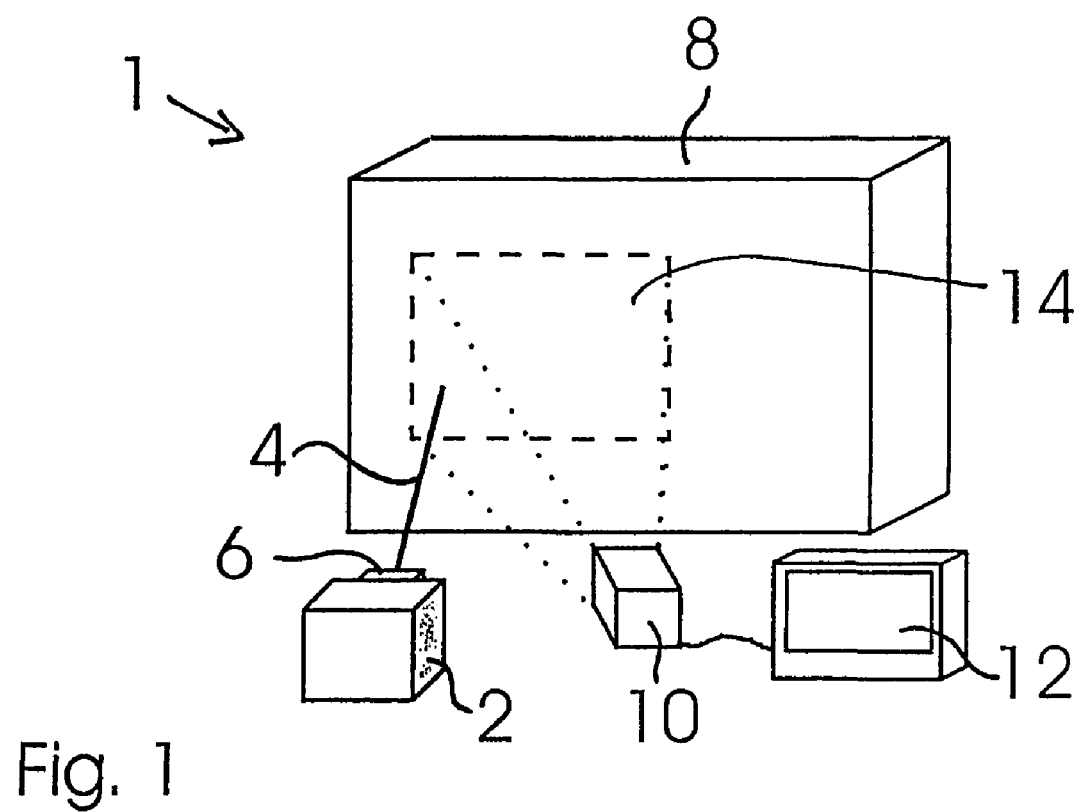
FIG. 1 is a schematic view of a device according to the present invention.

FIG. 1 shows the testing device 1 according to the present invention, comprising a laser device 2 which emits a laser beam 4 which is guided via a scan head 6 and then hits a test object 8. Further, a camera for determining and displaying as an image temperature differences (thermographic camera) 10 and an optional additional monitor 12 are shown. Said laser beam 4 is used to heat a test area 14 of the surface of said test object 8 facing said thermographic camera 10. Depending upon the size of the test object 8 to be tested, said test area 14 may cover the surface facing said thermographic camera 10 completely or partially.

The use of a diode laser device as laser device 2 has proved to be particularly beneficial, but other laser device types may be used as well. Said scan head 6 comprises one, two or more mirrors and is used to align and control said laser beam 4.

The selection of a suitable thermographic camera 10 should ensure the representation of temperature differences (threshold value) as small as possible within said test area 14. Good results were obtained using a camera of Messrs. FLIR Systems AB. This camera allows the representation of threshold values or temperature differences of 100 mK. further, this camera is capable of measuring temperature ranges from −40° C. to +120° C. (measuring range 1) or 0° C. to +500° C. (measuring range 2) and optionally temperatures up to 2,000° C. The detector used is a "Focal Plane Array (FPA)" infrared detector having an uncooled microbolometer with a resolution of 320×240 pixels and a spectral range from 7.5 to 13 µm. The frame frequency is 50/60 Hz PAL/NTSC non-interlaced. Field of vision angles from 7°×5.3° at a minimum focus of 6 m to 80°×60° at a minimum focus of 0.2 m and in case of close-ups from 64 mm×48 mm/150 mm or 32 mm×24 mm/80 mm can be accomplished. A 45°×34°/0.3 m lens achieved good results.

Figure 2:
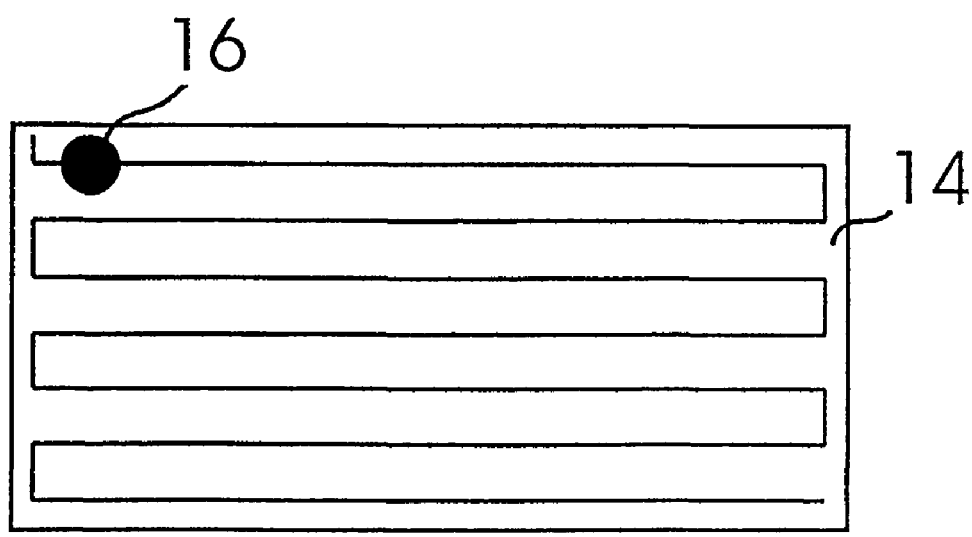
FIG. 2 is a schematic view of the scanning path of the laser beam.

A test object 8, for example made of GFP, is meandrically scanned by a diode laser having a wavelength of 808 nm and a scan head 6 with two mirrors for the x and y direction (cf. FIG. 2). Meandrical scanning ensures a defined and precisely repeatable scan of said test area 14. The wavelength of the laser beam may, depending upon the respective requirements, particularly upon the material, vary between 750 and 900 nm.

Said laser beam 4 may be focussed or not focussed by a lens depending upon the desired intensity and the area to be checked. The result of not focussing said laser beam 4 is a focal spot 16 covering an area of approximately 1.5 cm×1.5 cm. This focal spot 16 area, too, may vary corresponding to the respective requirements. The speed of said laser beam 4 or said focal spot 16 on said test object 8 may amount to 1 mm and 10 000 mm/s. Sufficient heating speeds of 100 mm/s for metal, 500 mm/s for GFP and 1,000 mm/s for polyethylene have proved as appropriate.

Any temperature change on the surface of said test object 8 can be observed in real time and simultaneously be recorded and/or stored, for example in an IMG format.

The targeted application of heat during some milliseconds onto the surface of said test object 8 makes any disturbances in the component to be tested immediately visible. Further heating processes allow the bringing-in of heat into said test object layer by layer.

A precise depth value of detected disturbances of any kind can be calculated as the time until the appearance of the disturbance, the amount of heat brought in (laser capacity), the area and the material are known.

As said scan head 6 may swivel in any direction, test objects 8 (components) may be tested in any position towards said laser device 2.

Figure 3:
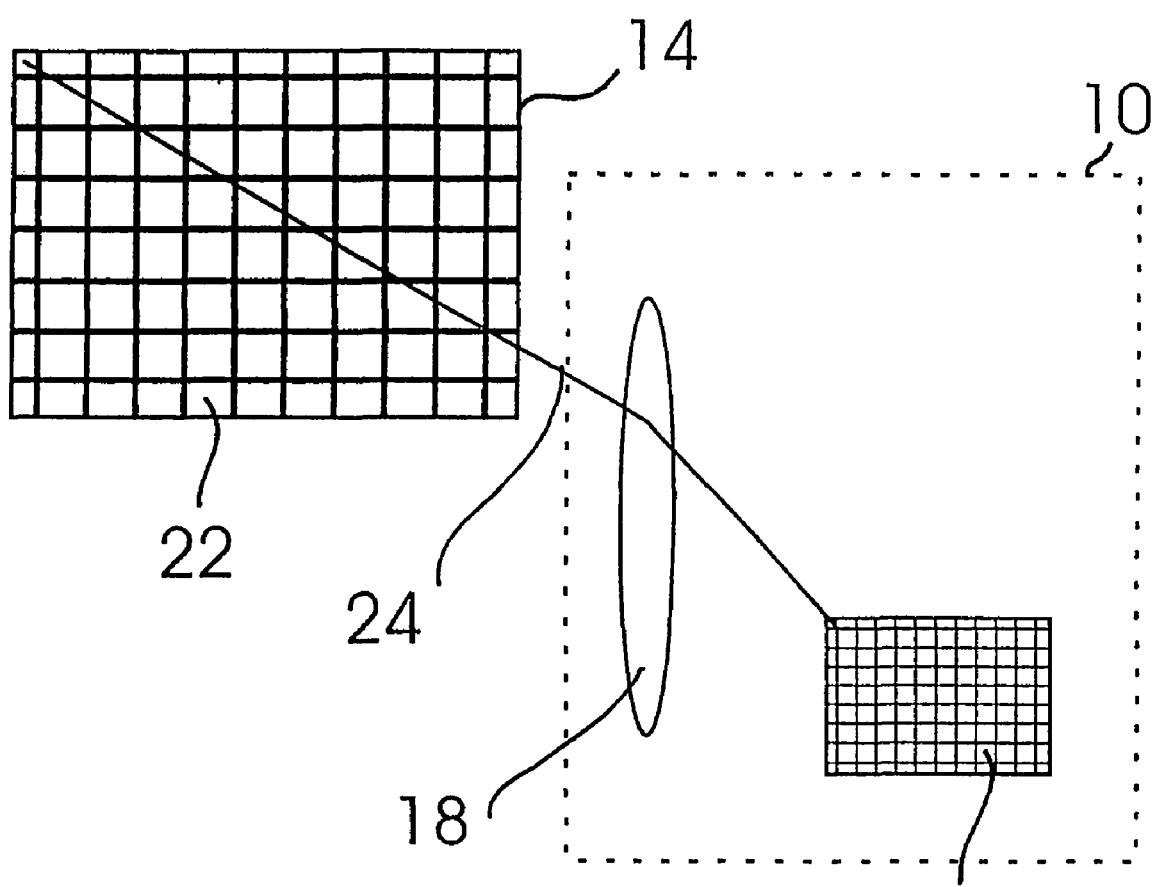
FIG. 3 is the principle of image display.

FIG. 3 illustrates the principle of image display. Said test area 14 is divided by said thermographic camera 10 (represented by dashed lines, a lens 18 and image elements 20) into object elements 22. The temperatures of said individual object elements 22 are determined by the camera and then displayed via a beam path 24 as image elements 20. The display may be in colour or grey scale, wherein a definite colour or a grey-scale value is allocated to each threshold value. The result is an image of said test area 8 represented on the basis of the temperature differences between said object elements 22. If said object elements 22 do not show any temperature difference, no contrast can be perceived on the display, for example on a monitor 12, based on said laser beam 4. Different temperatures of said object elements 22 are clearly discernible.

Figure 4A:
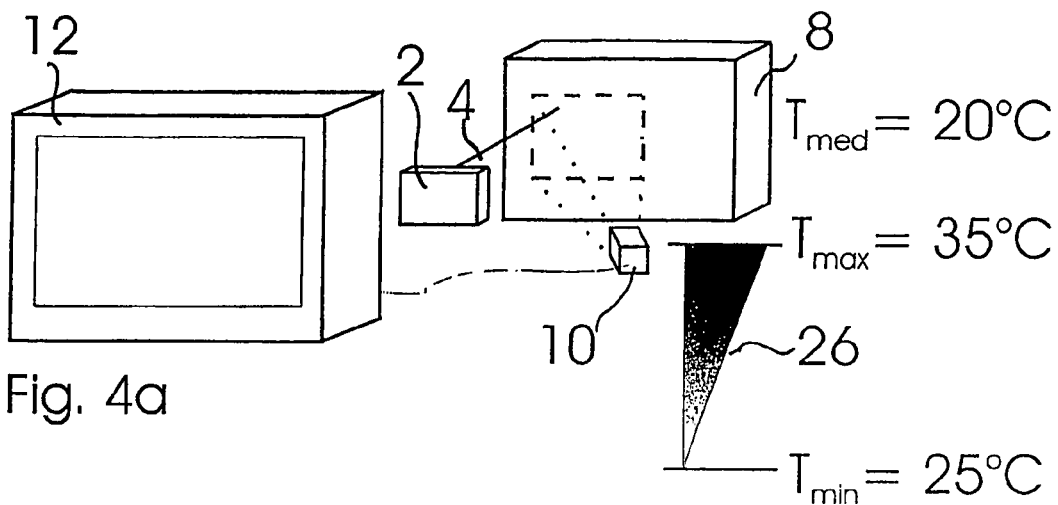
FIG. 4 is a simplified view of the performance of the testing method according to the present invention.
Figure 4B:
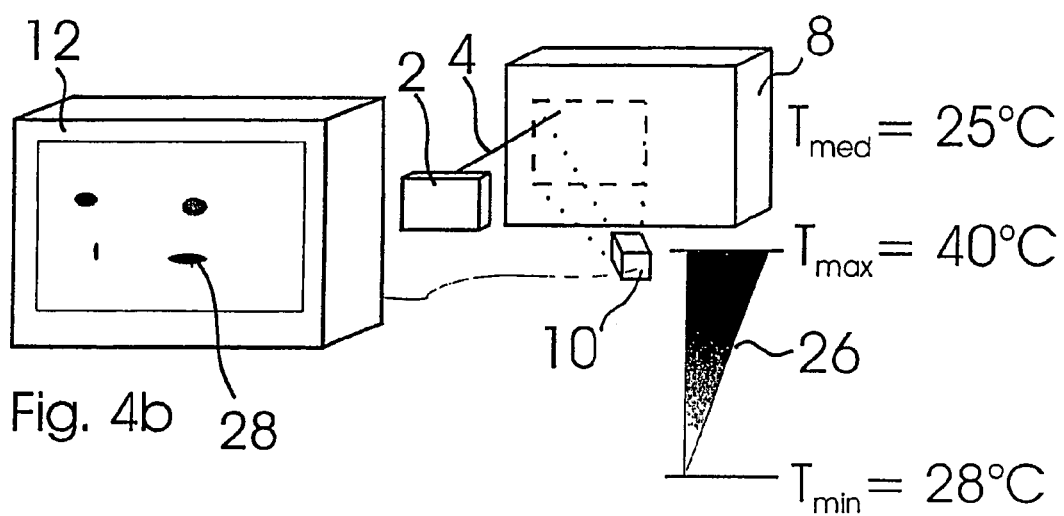
Figure 4C:
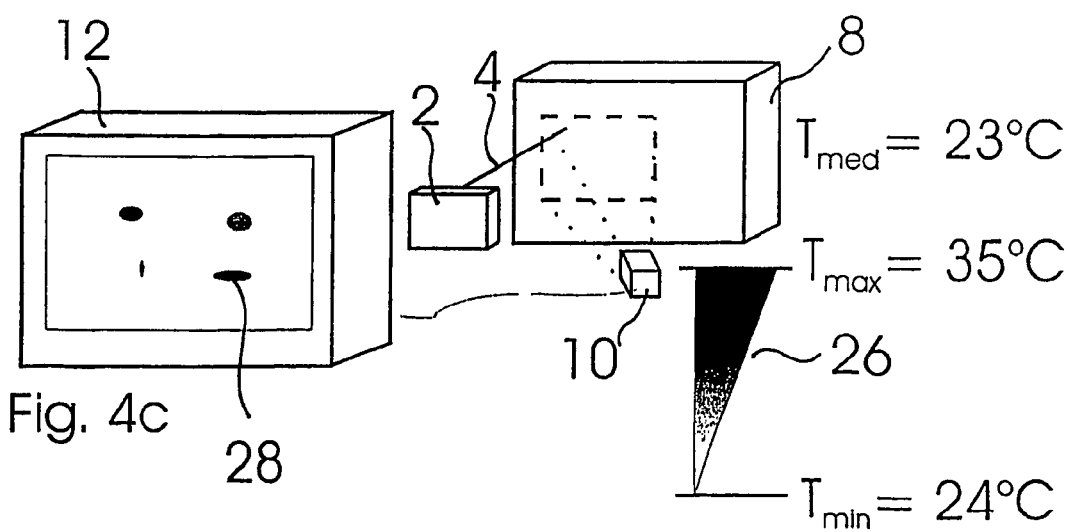

FIG. 4 illustrates the process of a test according to the present invention. In this example embodiment, said test object 8 keeps a thermal balance with the environment and has a surface temperature of 20° C. (see FIG. 4a). A grey-scale wedge 26 is shown aside said test object 8. Said grey-scale wedge 26 describes the representation of temperature differences (threshold values) by said thermographic camera 10. A coloured display instead of grey scales may be selected as well. It was found, however, that in many cases a grey-scale representation brings about better results. In typical thermography, low temperatures are represented dark and higher temperatures brighter. However, the inventors have found that an inverse representation brings about better results in testing materials. Thus, low temperatures are represented bright and higher temperatures darker.

According to the present invention, said thermographic camera 10 is adjusted in a first step in such a manner that the minimum temperature to be measured $T_{min}$ is higher than the average temperature $T_{med}$ (here 20° C.) of the test area to be tested. Here, the minimum temperature $T_{min}$ is 25° C. Starting from $T_{min}$, a so-called span is set which extends from said minimum temperature $T_{min}$ to the maximum temperature to be measured $T_{max}$ (here 35° C.). Thus, said test area 14 appears as a white area on said monitor 12. In a next step, said test area 14 is heated by means of said laser beam 4 in such a manner that the surface temperature of the test area rises by at least one and preferably several threshold values. In the present example, the medium temperature $T_{med}$ rises to 25° C. Immediately, areas within said test area 14 become visible which deviate from said average temperature $T_{med}$. such disturbances 28 appear as dark spots on said monitor 12 when they have a higher temperature than $T_{med}$. As the average temperature $T_{med}$ has also risen compared with the initial temperature due to heating, the entire test area 14 appears also darker. In order to achieve a clearer representation of said disturbances 28, the grey-scale wedge 26 controlling the representation on said monitor 12 is adapted to the now higher average temperature $T_{med}$ by increasing the minimum temperature $T_{min}$ to be represented until it becomes equal to or higher than the average temperature $T_{med}$. Thus, said test area 14 is again displayed as a white area on said monitor 12 while only said disturbances 28 which impair the carrying-off of heat appear as easily discernible dark spots (cf. FIG. 4b).

If no more thermal energy is supplied to said test object 8, said test object 8 cools down, or heat flows into said test object. This is visible on the surface of the test object or said test area 14 due to the developing or changing temperature differences on the surface. This is particularly facilitated when said grey-scale wedge 26 is consistently adapted to the medium temperature $T_{med}$. For this purpose, said thermographic camera 10 permanently determines the average temperature $T_{med}$ which is lowering due to the heat discharge and adapts said grey-scale wedge 26 in such a manner that the average temperature $T_{med}$ is represented as white (FIGS. 4b and c). In this manner, for example, air inclusions impairing the heat flow into said test object 8 can be localised as dark areas. The recording of the changes of the surface temperature in said test area 14 over a definite period of time allows the calculation and representation of a three-dimensional image of said test area 14 or said test object 8. The essential material specifications allow the determination of the position and extension of disturbances 28 within said test object 8. In order to facilitate the representation of those disturbances 28 which promote the heat flow into said test object 8, such as metallic inclusions in glass-fibre plastic plates, said grey-scale wedge 16 is to be adjusted so that those areas which have a higher temperature than the average temperature $T_{med}$ are visible as well. This can be accomplished in particular by representing the average temperature $T_{med}$ as a medium grey colour and the disturbances 28 promoting the heat flow as correspondingly brighter areas. It is thus possible to adapt said grey-scale wedge 26 in such a manner that those disturbances 28 which promote the heat discharge as well as those which impair the heat discharge are both visible.

Depending upon the actual application, said grey-scale wedge 26 may also be adapted so that either only disturbances 28 which promote the heat discharge or only disturbances 28 which impair the heat discharge are displayed. The adaptation of the display to the average temperature $T_{med}$ may be performed manually instead of an automatic permanent adaptation. It is imaginable as well to equip said thermographic camera 10 with a marking device for marking within said test area 8. This may be accomplished, for example, by a targeted ink or colour jet. Depending upon the application case, other marking methods are possible as well, such marking is especially useful when said test objects 8 are to be further processed or repaired after the test.

It has proved to be particularly advantageous to record said test object 8 at first in its original state followed by its heating and subsequent cooling-down of said test object 8 as a consecutive sequence like a video film by means of said thermographic camera 10. This will provide a documentation of all states from the original state to the state after cooling down. This film which should be digitised if possible can then be further processed in a computer 30 using appropriate software. For example, the grey portions of said grey-scale wedge 26 may be adapted to improve contrast. A good representation of the temperature changes of said test area 14 is accomplished by playing a certain film sequence at a higher speed several times or infinitely (so-called loop play). An appropriately high frame repeat rate provides a practically immobile image in which the components or material differences affecting the heat discharge are well visible. It is also possible in a good and easy manner to put digitised data generated in this manner into archives.

Figure 5:
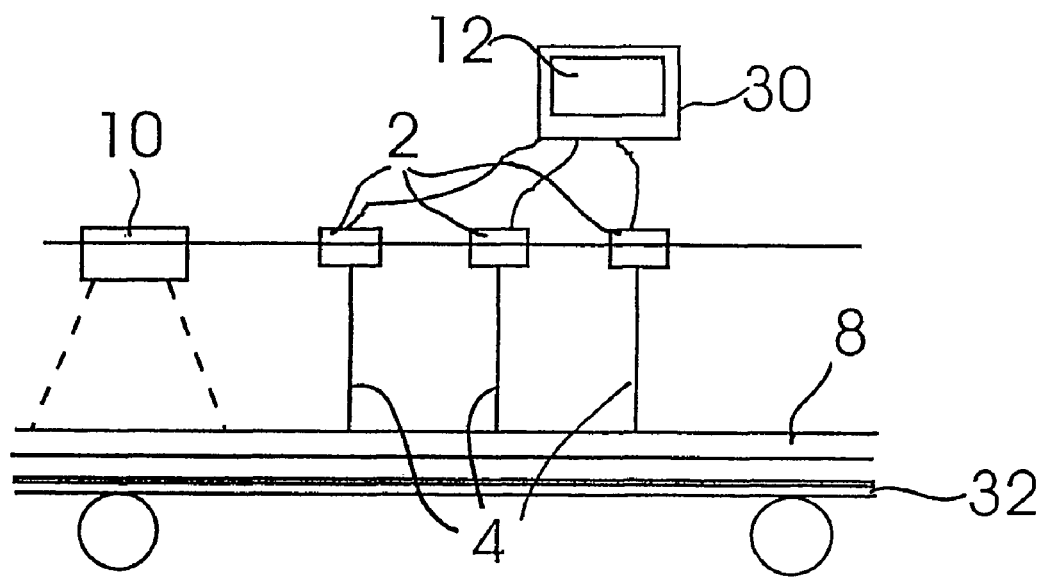
FIG. 5 is a schematic view of an automated checking means.

FIG. 5 shows that the method or device according to the present invention may also be used in an automated process. For example, test objects 8 positioned on a belt conveyor 32 may be fed towards said laser device 2 or said laser beam 4 which at first heats said test objects 8. Then, said test objects 8 are advanced to a thermographic camera 10 which measures their surface temperature. In order to ensure measurement over a longer period of time, said thermographic camera 10 may be movably arranged on a rail 34 so as to move parallel to the conveyor belt and at the same speed. The adjustment of, for instance, the grey-scale wedge 26 is performed fully automatic, and the determination of the measuring data or their representation and evaluation is performed by a computer 30 connected to said thermographic camera 10 and equipped with a monitor 12. Faulty test objects 8 can be identified and sorted out. In order to ensure a sufficient speed of the test process, it may be useful to arrange several thermographic cameras 10 which check areas of said test objects 8 in sequence.

Figure 6:
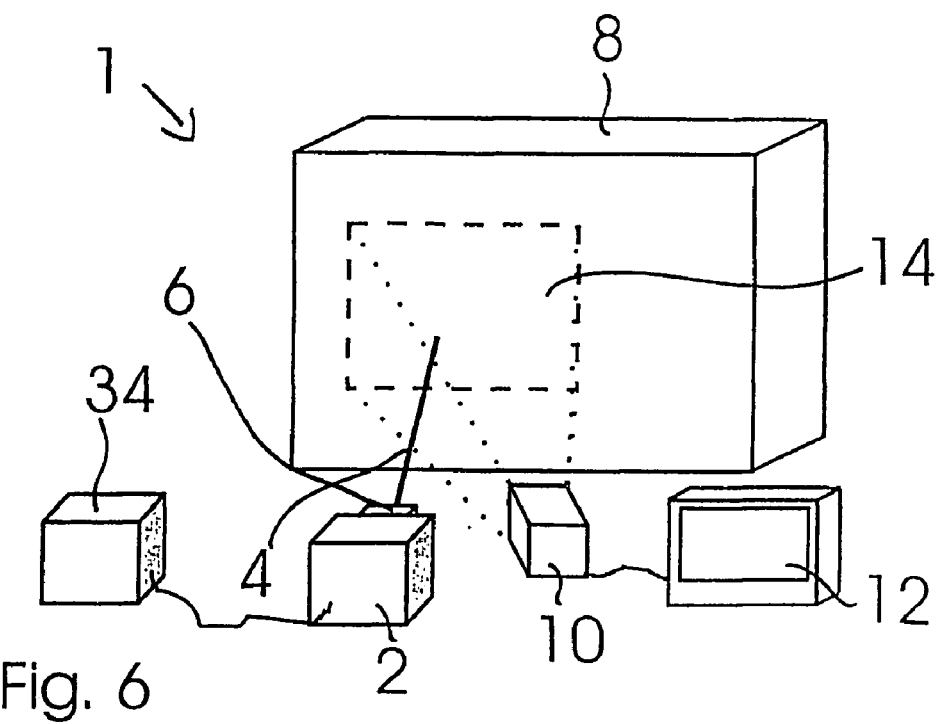
FIG. 6 is a schematic view of a device according to the present invention comprising an additional camera for recording the reflections of the test area.

It is possible as well to improve the investigation of the test object by, for example, previously determining the heat absorption capability of the test area. As shown in FIG. 6, a CCD camera 34 is provided in addition to record the reflected image of the test area 14 after its entire surface has been heated for a short time. The resulting image (photograph) shows high reflection areas bright and low reflection areas darker. The subsequent heat supply by the laser which in the end is to serve the investigation of the test area, may then be properly adjusted through the intensity or resting duration of said laser beam 4 to achieve an even heating of the deeper layers independent of the surface of the test area 14. For this purpose, a direct connection or feedback between the CCD camera and said laser device 2 may be provided.

The reflected share and thus the absorbed share of a first heating for later adjusting the supply of heat may also be measured by the thermographic camera itself. Immediately after the first heating, the test area is recorded by the thermographic camera. The resulting image also shows those spots or portions of the test area which reflect or carry away heat to a larger or smaller extent.

The present invention is not restricted to the example embodiments described but includes any testing methods acting in the sense of or using this invention. The representation of the test results may, for example, be performed in different manners depending upon the design of said thermographic camera 10, for example, a coloured or more or less resolved display corresponding to the test object 8 may be useful. This testing method is suitable for contactless, non-destructive testing of test objects 8 in the broadest sense of the word. The utilisation of this testing method in the medical field is imaginable as well.

With regard to heat supply, it is also possible to use the Peltiers effect instead of or in addition to a light beam or said laser beam 4. When the two ends of a metal piece (or a semiconductor) are brought into contact with another metal piece and an electric direct current is conducted through them, one contact point heats up while the other cools down. When the current direction is reversed, the warm and cold points are also interchanged. So it is not a temperature difference which generates a current, but the supply of a direct current establishes a temperature gradient which can be determined and/or checked by using the method or device according to the present invention. The Peltiers effect may, for example, be used to check the quality of weld seams.

Said test object 8 may also be heated by induction heating. The rapid change of a magnetic field induces vortex currents in conductive materials. The current flow causes a voltage drop at the inherent resistance of the material which may be used to transfer power. Thus, the material heats up in itself without direct supply of thermal energy. This type of heating might, for example, be used in the investigation of steel structures such as bridges or towers.

The method according to the present invention may further be applied in such a manner that only partial areas of the surface of said test object 8 are selectively heated up or cooled down. The subsequent temperature expansions allows conclusions regarding material properties. Ideally, heat spreads in a homogeneous body in a circular way starting from the heating point. If, however, a crack or a material inclusion exists in the range of heat spreading, the even, circular heat spreading is disturbed. The method according to the present invention allows a clear determination of such heat gradients and thus anomalies.

The device and the method according to the present invention are easy to implement and are suitable for investigating a plurality of objects or materials. It is possible, for example, to check banknotes quickly and simply. Banknotes consist of different materials and thus have a characteristic behaviour in case of temperature changes which behaviour can be determined by the method according to the present invention. It is possible for example, to store this "correct" behaviour in a computer and to compare the temperature behaviour of a banknote to be tested with this reference behaviour. Deviations would then indicate counterfeit money.

The invention claimed is:

1. A method for determining and localizing the position and extension of disturbances within a test object by means of a thermographic camera which determines temperature differences above a definite threshold value, wherein temperature differences on a surface of the test object are determined and displayed as an image, wherein
   the individual temperatures of object elements defined within a test area of the surface of said test object facing the camera are determined and displayed,
   the object elements are displayed as image elements in such a manner that their individual temperature behaviour becomes discernible due to temperature changes in comparison to an average temperature $T_{med}$ of all the object elements,
   before the beginning of the testing, the test object is at an average temperature $T_{med}$ winch is in thermal balance with the environment, therefore the displayed image elements do not show any differences among each other,
   said method comprising:
   a) actively changing the temperature of said object elements within said test area and accordingly the avenge temperature $T_{med}$ several times during a period of time by means of a laser beam, in such a manner that in each case the temperature of the surface of the test area changes by at least the amount of the threshold value, and
   b) technically measuring the amount of heat absorbed by the surface and recording it intermediately following supply of heat to the object elements by the laser beam,
   c) permanently determining the average temperature $T_{med}$ of the test area during the period of actively changing the temperature,
   d) adapting the display of the object elements in such a manner that the changing average temperature $T_{med}$ during the period of actively changing the temperature is displayed during the whole period of time in the same manner as before the beginning of the active change of the temperature,
   e) recording the change of temperature of the surface of the test area during the period of actively changing the temperature, and
   f) calculating and determining the position and extension of disturbances within said test object using data of the recorded change of temperature of the object elements of the test area; and
   wherein a reflected image is determined by the thermographic camera, while during another subsequent supply of heat, differing reflection capabilities of individual or several object elements are determined and equalised by heat supply of correspondingly differing intensities in such a manner that a homogeneous heat supply into the depth of said test object is accomplished.

2. The method according to claim 1, wherein said laser beam is emitted from a diode laser device and is guided via a scan head.

3. The method according to claim 1, wherein a focal spot of said laser beam is guided meandrical at a speed from 1 to 10,000 mm per second across the surface of said test object.

4. The method according to claim 1, wherein the temperatures of said object elements are determined by means of said thermographic camera intermediately following the supply of heat, while during another subsequent supply of heat, differing heat absorption capabilities of individual or several object elements are determined and compensated for by heat supply of correspondingly differing intensities in such a maimer that a homogeneous heat supply into the depth of said test object is accomplished.

5. The method according to claim 1, wherein the temperature change of said test area is displayed on a monitor screen in real time using said image elements.

6. The method according to claim 1, wherein the beating of individual object elements is performed for less than one second.

7. The method according to claim 6, wherein the heating of the individual object elements is performed for less than a tenth of a second.

* * * * *